(12) United States Patent
Haselhuhn et al.

(10) Patent No.: US 8,465,281 B2
(45) Date of Patent: Jun. 18, 2013

(54) IMPRESSION TRAY

(76) Inventors: Klaus Haselhuhn, Aachen (DE);
Jan-Dirk Reimers, Aachen (DE);
Hubertus Spiekermann, Haan (DE)

( * ) Notice: Subject to any disclaimer, the term of this patent is extended or adjusted under 35 U.S.C. 154(b) by 1201 days.

(21) Appl. No.: 11/579,707

(22) PCT Filed: May 3, 2005

(86) PCT No.: PCT/EP2005/004794
§ 371 (c)(1),
(2), (4) Date: Jan. 17, 2007

(87) PCT Pub. No.: WO2005/107632
PCT Pub. Date: Nov. 17, 2005

(65) Prior Publication Data
US 2008/0286714 A1      Nov. 20, 2008

(30) Foreign Application Priority Data

May 5, 2004   (DE) .................. 10 2004 022 066

(51) Int. Cl.
*A61C 9/00*        (2006.01)
(52) U.S. Cl.
USPC ............................................. 433/37
(58) Field of Classification Search
USPC ....................... 433/37, 43, 173, 174
See application file for complete search history.

(56) References Cited

U.S. PATENT DOCUMENTS

| | | | |
|---|---|---|---|
| 4,708,654 A | 11/1987 | Branemark et al. | |
| 4,763,791 A * | 8/1988 | Halverson et al. | 206/570 |
| 4,842,515 A | 6/1989 | Zeiser et al. | |
| 5,403,185 A * | 4/1995 | Presswood | 433/74 |
| 5,466,152 A * | 11/1995 | Walter | 433/74 |
| 5,636,985 A * | 6/1997 | Simmen et al. | 433/37 |
| 6,379,147 B1 * | 4/2002 | Georgakis et al. | 433/37 |
| 6,428,315 B1 * | 8/2002 | Prestipino et al. | 433/45 |
| 6,468,078 B2 | 10/2002 | Guillaume et al. | |
| 6,508,650 B2 * | 1/2003 | Gittleman | 433/172 |
| 6,629,841 B1 | 10/2003 | Skinner | |
| 6,666,684 B1 | 12/2003 | Names | |
| 2002/0127515 A1 | 9/2002 | Gittleman | |
| 2003/0138754 A1 | 7/2003 | Dimarino et al. | |

FOREIGN PATENT DOCUMENTS

DE           42 18 423          12/1993

OTHER PUBLICATIONS

Definition of Penetrate retrieved from: http://www.merriam-webster.com/dictionary/penetrate on Mar. 11, 2010.*

* cited by examiner

*Primary Examiner* — Heidi M Eide
(74) *Attorney, Agent, or Firm* — Collard & Roe, P.C.

(57) ABSTRACT

Disclosed is an impression tray (1) with a concave tray body (2) for taking an impression of at least one jaw part, in which at least one implant body (12) is situated, which body has a receiving aperture into which an impression post (11) may be inserted, it being possible to fill the impression tray (1) with a free-flowing hardenable impression material (10) to produce a mold for a model of the jaw part, which when used reduces the time spent in the dentist's chair, increases the precision of an implant model and finally reduces the material and labor costs in that, at least in one portion, the tray body (2) has a wall (6, 6') which can be penetrated by an impression post (11) inserted into the implant body (12) if the impression tray (1) is placed onto the jaw part.

4 Claims, 4 Drawing Sheets

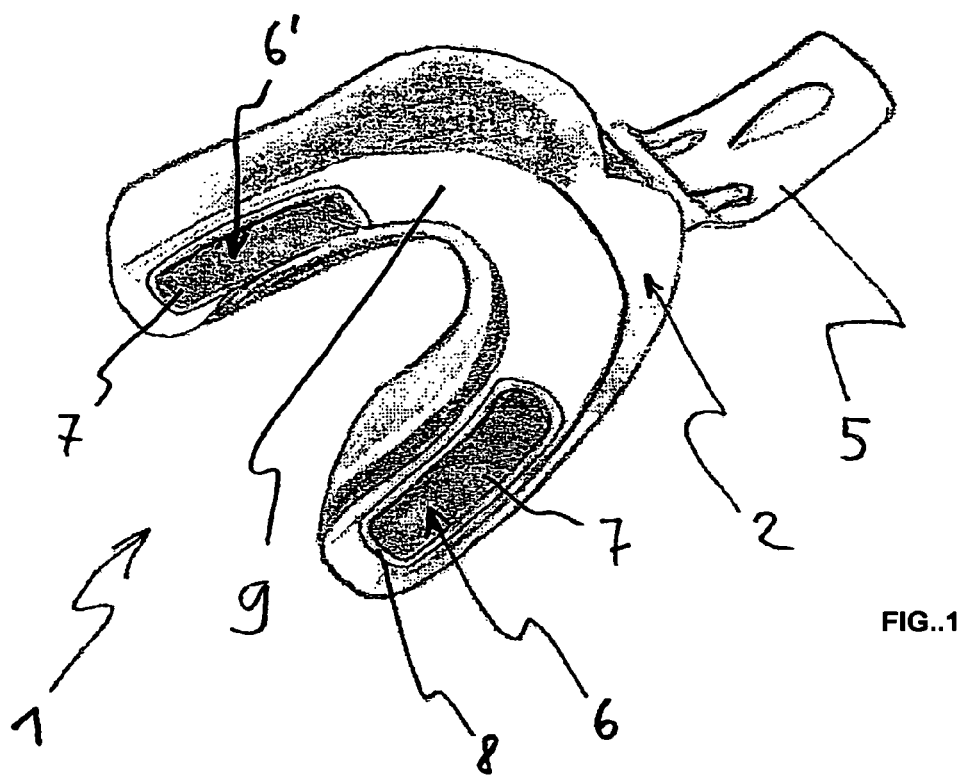
FIG..1

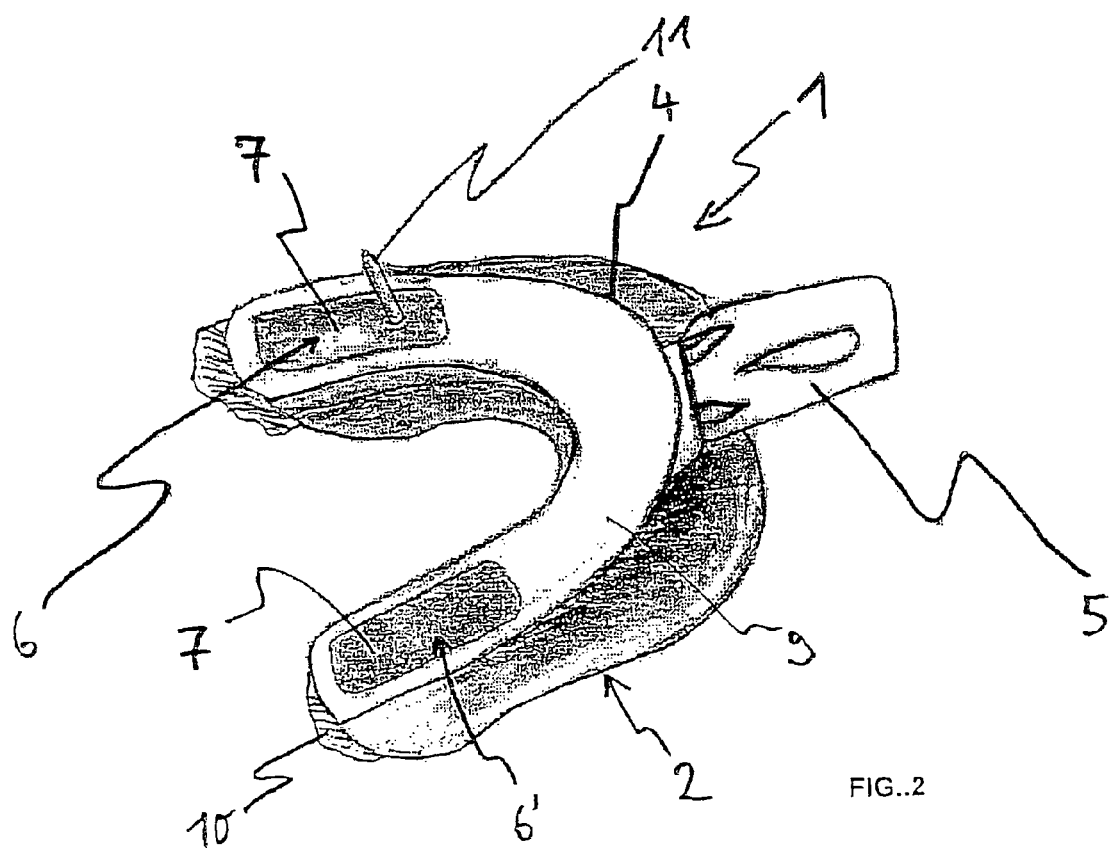
FIG..2

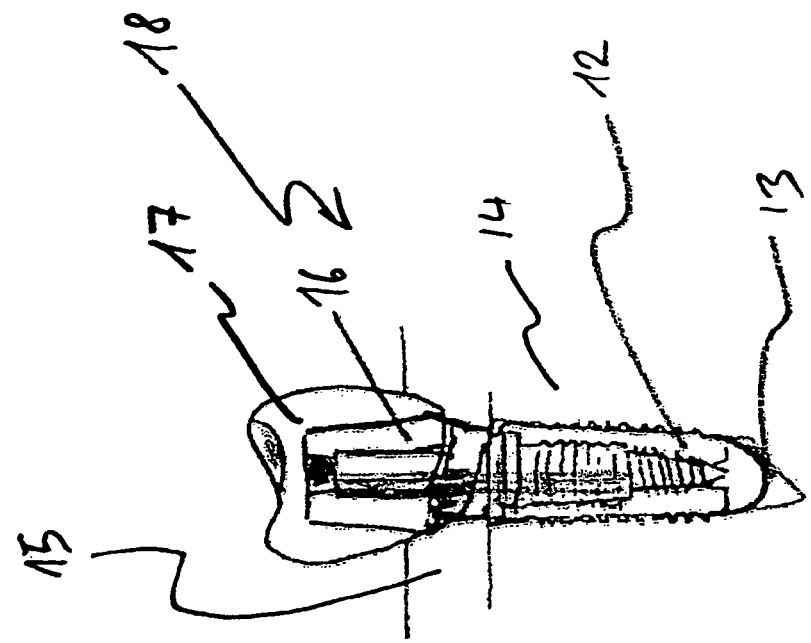
FIG..4
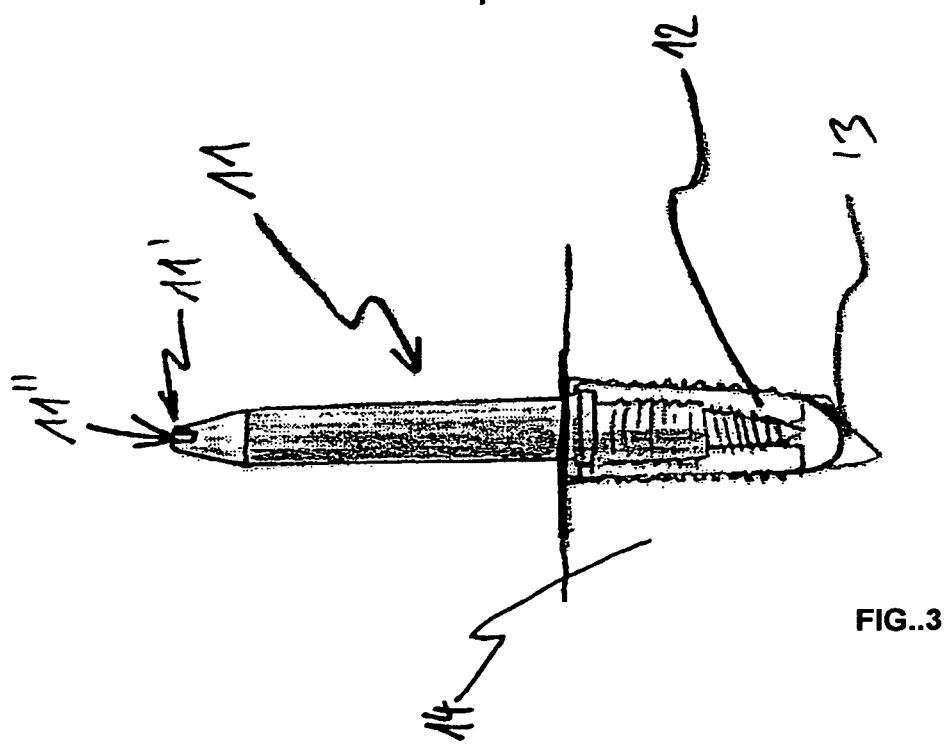
FIG..3

IMPRESSION TRAY

CROSS REFERENCE TO RELATED APPLICATIONS

Applicants claim priority under 35 U.S.C. §119 of European Application No. DE 10 2004 022 066.2 filed May 5, 2004. Applicants also claim priority under 35 U.S.C. §365 of PCT/EP2005/004794 filed May 3, 2005. The international application under PCT article 21(2) was not published in English.

BACKGROUND OF THE INVENTION

1. Field of the Invention

The invention relates to an impression tray with a concave tray body for taking an impression of at least one jaw part, in which at least one implant body is situated, which body has a receiving aperture into which an impression post may be inserted, it being possible to fill the impression tray with a free-flowing hardenable impression material to produce a mould for a model of the jaw part.

2. Description of the Related Art

As is known, when one or more teeth are lost replacement roots, what are known as implants, are implanted into the jaw. These supports that are anchored in the jaw form the stable base for new, secure teeth. The size and shape of an implant is guided by the individual preconditions of the jaw of the patient being treated. One precondition for tooth implantation is a minimum jaw bone substance.

Since implants are osseo-integrated (anchored to a bone) and, in contrast to natural teeth, do not—ideally—have even the slightest inherent movement, when constructing a plurality of implants an optimally exact three-dimensional reproduction of the position of the individual implants is particularly important.

The replacement produced in a dental laboratory can only be successfully incorporated in the oral cavity without stress if the clinical situation is transferred exactly to a model. While a precise impression is not a sufficient condition it is a necessary one for implantological-prosthetic care.

The aim of any impression is thus the exact dental model. It is used for diagnosis, planning and treatment purposes as well as a work basis for the dental technician and should be an exact copy of the structures that are in the oral cavity.

The part of an implant system that is countersunk into the bone is either called an implant body or simply an implant. Once it has been introduced into the bone the hollow implant body is provided with a cover screw. The gums are then stitched over the implant body. Following a healing phase of several months' duration, the doctor then exposes the implant body again, removes the cover screw and temporarily screws or inserts an impression post in its place.

After a healing period of 10 to 14 days, the impression may be taken over the impression post by means of an individually shaped impression tray in order to subsequently produce the crown, bridge or prosthesis. The impression post is then replaced for a few days by healing abutments. The definitive new teeth are not secured directly to the implant bodies, but to implant superstructures, however. Implant superstructures bridge the thickness of the gums, so the gums cannot be squashed between implant body and prosthesis. The healthy gums attach to these implant superstructures as to a natural tooth. The prosthesis accordingly supported by the implant abutment and implant body is called a superconstruction and is secured by filling screws or other fastening principles to the individual implant bodies.

To determine the three-dimensional position of the implant body and to transfer this to the final laboratory model, the following steps are carried out:

1. Taking a negative impression of a jaw, or jaw part, by means of a standardised impression tray, a cover screw, arranged inside the impression tray, being screwed into the implant body,
2. a) Producing a first laboratory model using the negative impression,
   b) Producing an individual impression tray using the laboratory model, the impressions of the cover screw being drilled in order to allow subsequent passage of an impression post through the impression tray at this location.
3. a) Removing the implant cover, anchoring a multi-part impression post in the jaw by latching or screwing,
   b) Filling the impression tray with impression material in the region of the hole,
   c) Placing the impression tray on the jaw, with the impression post surrounded by the impression material projecting through the hole and beyond the impression tray,
   d) Once the impression material has hardened, unscrewing, removal or detachment of the impression post and removal of the impression tray with the impression material, an impression post sleeve that laterally surrounds the impression post remaining in the impression material.
4. a) After disinfecting the impression tray, producing a second laboratory model, with a laboratory implant body being placed on or screwed to the impression post sleeve in the impression material by means of a laboratory impression post. The material for moulding the second laboratory model is injected onto the laboratory implant body. The remaining negative mould of the laboratory model is filled with model materials, such as plaster of Paris or plastics material. After the model materials have hardened the impression post retaining screw or the impression post retention pin can be detached again. The impression tray can be removed from the model.
   b) Choosing and using a suitable implant abutment in the laboratory implant body of the second laboratory model, production of the dental prosthesis.

The repositioning technique may be used as an alternative. The major advantage is that the patient is spared a treatment appointment for production of the individual impression tray. A further advantage is also that the costs that occur during production of the individual impression tray with respect to expenditure of material and time do not apply in the case of the repositioning technique with ready-made trays.

However, a drawback of this technique is that its application is error-prone and has also been proven to be less precise compared with the above-described "pick-up" technique since, inter alia, the channel-like impression of the impression post required for the three-dimensional repositioning of the position of the implant body in the impression material may only be replaced by shallow and imprecise impressions of impression elements and hence leads to unsatisfactory results for the doctor and primarily the patient. Repositioning of the impression tray also leads to significant movements in the impression material, so the precision of the subsequent model decreases.

Guillaume et al disclose in U.S. Pat. No. 6,468,078 B2 a ready-made tray comprising a plurality of removable segment seals. Depending on the position of the impression post—which is constructed as a sleeve—it is proposed that the segment seal located thereabove be removed and the material, which is still covering the impression post and a screw fixing the post to the implant body, subsequently be removed until at least the screw head is completely exposed. After the impression material in the ready-made tray has hardened the screw should be detached. The impression post remains in the impression material moreover and is used to fix the laboratory implant using the impression screw.

When using the proposed impression tray however the process of removing impression material over the screw, which process on its own is already complex but, owing to hardening of the impression material, is also limited in terms of time, may lead to considerable problems. The exact position of the screw must also firstly be ascertained and then the screw head freed of the impression material, at least to the extent that the screw may be engaged using a screwdriver or the like. A further drawback is that the interplay between impression post and positioned impression tray may no longer be checked and corrected if necessary since the impression post can no longer be seen in its position relative to the impression tray.

SUMMARY OF THE INVENTION

The object of the invention is to propose an impression tray which when used reduces the time spent in the dentist's chair, increases the precision of an implant model and finally reduces the material and labour costs.

The object is achieved according to the invention in that, at least in one portion, the tray body has a wall which can be penetrated by an impression post inserted into the implant body if the impression tray is placed onto the jaw part.

The advantages of the respective known impression taking techniques are combined by the invention. On the one hand production of an individual impression tray may be omitted in that the impression tray according to the invention is produced as a ready-made "disposable or reusable serial tray" in appropriate standard sizes. On the other hand, implant impression taking may still be carried out using the precise pick-up technique that is much favoured, since the walls of the impression tray, usually the base wall, can easily be penetrated by the impression post. This is advantageous because, as a result, the impression post can be removed again after the impression material has cured and the finished impression can be removed from the mouth. Impression material is also effectively prevented from escaping with the adverse effects associated therewith.

As a result of simple handling and safety the impression tray according to the invention results in a time saving which is of benefit to both the dentist and the patient.

In addition, a cost reduction therefore already results due to the fact that previously hand-made unique copies are replaced by serial products.

And not least of all, dental procedures that are harmful to health, as occur in the production of individual impression trays as a result of the production of silica dust, are avoided.

One development of the invention is that the impression tray comprises struts, which form a frame, and a membrane located therebetween to thus allow the greatest possible variability with respect to the possible implant placements and the implant orientation while still having a stabilising frame.

Another development of the invention is that for an improved penetrating capacity of the impression material and the wall of the impression tray, the impression post comprises a final shape that is beneficial to penetration, for example tapers or cutting edges, or a removable cap with a corresponding final shape. Obviously the scope of the invention also extends without any limitations to the field of veterinary medicine since all illustrated advantages benefit animals and their owners equally as well.

With another development of the invention, the impression tray may be a plastics material injection molded part integrally joined with a penetrable portion thereof, with the penetrable portion being any of a membrane, a woven fabric, a non-woven fabric, and a film.

BRIEF DESCRIPTION OF THE DRAWINGS

The invention shall be described hereinafter with reference to an embodiment.

In the drawings:

FIG. 1 shows a perspective view of the side of an impression tray according to the invention that is to be filled with impression material, FIG. 2 shows the impression tray according to FIG. 1 but from the other side, and a portion of an impression post, FIG. 3 shows a partially perspective section through an implant body and an impression post according to the invention, and FIG. 4 shows a partially perspective section through a two-phase cylinder implant.

DETAILED DESCRIPTION OF THE PREFERRED EMBODIMENTS

Figure 5:
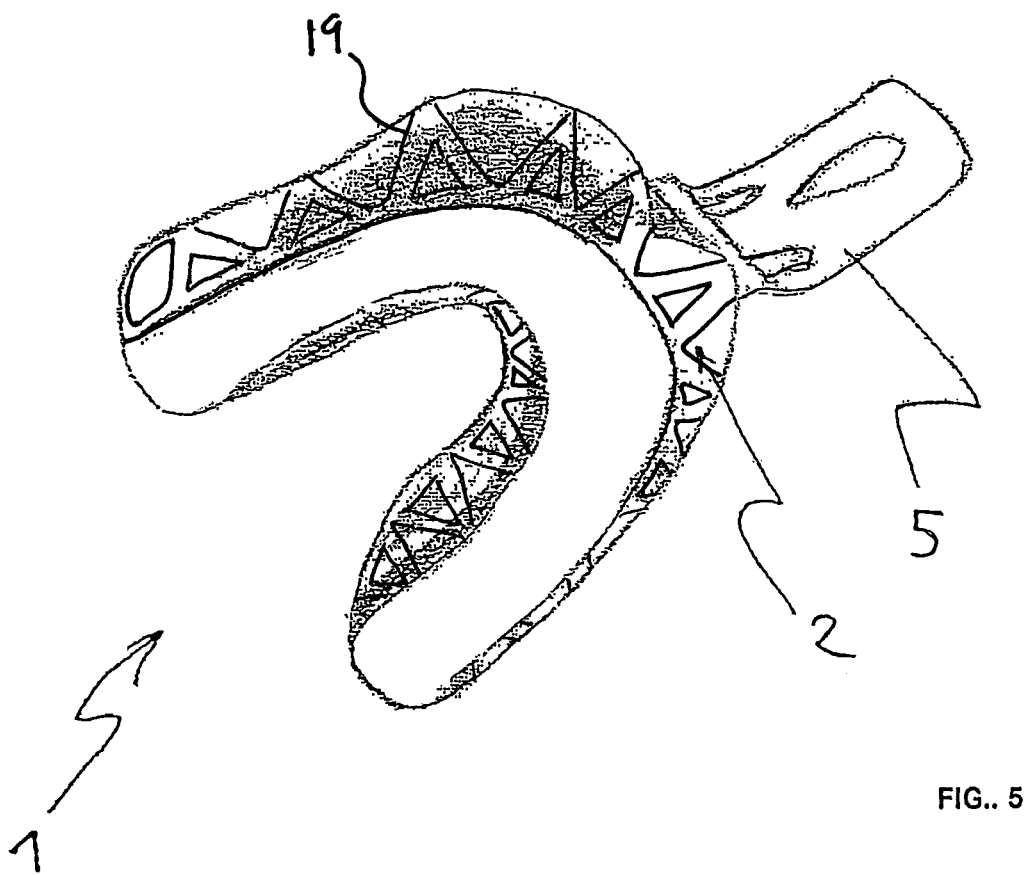

The one-piece impression tray 1 illustrated in FIG. 1 and FIG. 2 that is made of plastics material, in particular of two-component injection moulded plastics material, comprises a concave impression body 2 that is adapted to a jaw or jaw part and to the lateral edge 4 of which a tray handle 5 adjoins. At the left-hand and right-hand sides of the impression body 2 there are portions of the wall 6, 6' with a particularly thin wall thickness constructed as a film 7 or membrane made of the same plastics material as the rest of the impression body 2. The transition from the otherwise approximately two to four millimeter thick wall 9 of the impression body 2 up to the approximately only 200 micrometer thin film 7 is formed by a transition region 8 that is approximately two millimeters wide.

FIG. 2 is intended to illustrate the use of the impression tray 1 according to the invention. The impression tray 1 is partially filled with impression material 10 and has been firmly pressed into its end or hardening position on a jaw (not shown here) with an implant body 2 (likewise not shown) inserted into the jaw and an impression post 11 screwed therein. In the portion of the wall 6 the impression post 11 has locally penetrated the film 7 to a limited extent without impression material 10 having continued to flow. An impression post sleeve that is required for subsequent precise positioning of a laboratory implant body and that laterally surrounds the impression post 11 is not shown.

FIG. 3 again shows the impression post 11 according to the invention with taper 11' and slit 11", screwed into an implant body 12 which has been introduced into a hole 13 in the jawbone 14. A removable cap according to the invention, which owing to its taper, for example in the form of a cone, can penetrate impression material and wall 6, 6' of the impression tray 1 particularly easily, is not shown.

FIG. 4 shows a known cylinder implant 18, which has healed in the jawbone 14 and gums 15, comprising the implant body 12, an implant abutment 16 and the crown 17 sitting thereon.

In alternatives according to the invention (not shown here) different material is provided for the impression tray 1 and the film 7. The impression tray 1 may therefore also be made of metal which comprises apertures in the region of the wall 6, 6' that is still covered by film 7, non-woven fabric or laminated woven fabric. For this reason a conventional metal, ready-made tray, if it has a recess which is covered with conventional adhesive tape, for example single-sided tape, obviously also falls within the scope of the invention.

Alternatives in which the penetrable wall 6, 6' can take up a complete wall region of the impression tray 1, such as the base region of the impression tray 1, are not shown either.

A further alternative (not shown) is that curved coverings or penetrable walls 6, 6' are used in the case of an extremely oblique position of the implants 18. Alternatives that relate to variations in joining the penetrable wall 6, 6' and impression tray 1 are not shown either. Thus for example the penetrable wall 6, 6' can be secured to the impression tray 1 from the inside and from the outside using overlapping regions of different widths. Securing may be achieved here for example by gluing or by mechanical fixing and/or jamming.

LIST OF REFERENCE NUMERALS

1 impression tray
2 impression body
4 lateral edge
5 impression handle
6, 6' wall
7 film
8 transition region
9 wall
10 impression material
11 impression post
11' taper
11" slit
12 implant body
13 hole
14 jawbone
15 gums
16 implant abutment
17 crown
18 cylinder implant

The invention claimed is:

1. A combination comprising:
   (a) an impression tray comprising a concave tray body for taking a negative impression of at least one jaw part in a mouth of a patient;
   (b) an impression post; and
   (c) at least one implant body that is adapted to be situated in the at least one jaw part, said at least one implant body comprising a receiving aperture for insertion of the impression post;
   wherein the tray body is fillable with a free-flowing hard-enable impression material to produce a mold for a model of the at least one jaw part; and
   wherein the tray body comprises a wall having at least one penetrable portion for penetration by the impression post inserted in the at least one implant body when the tray body is placed onto the at least one jaw part; and
   wherein the at least one penetrable portion of the wall is a membrane, a woven fabric, a non-woven fabric or a film.

2. The combination according to claim 1, wherein the at least one penetrable portion of the wall is a membrane and the membrane is self-adhesive.

3. The combination according to claim 1, wherein the impression tray is a plastics material injection molded part comprising the at least one penetrable portion integrally joined thereto and penetrable by the impression post.

4. A dental set comprising
   (a) an impression tray comprising a concave tray body for taking a negative impression of at least one jaw part in a mouth of a patient and at least one implant body that is adapted to be situated in the at least one jaw part, said at least one implant body comprising a receiving aperture; and
   (b) at least one impression post insertable into the receiving aperture of the at least one implant body;
   wherein the tray body is fillable with a free-flowing hard-enable impression material for producing a mold for a model of the at least one jaw part;
   wherein the tray body comprises a wall having at least one penetrable portion for penetration by the at least one impression post inserted in the at least one implant body when the tray body is placed onto the at least one jaw part; and
   wherein the at least one impression post comprises at least one of a taper, a cutting edge, a removable cap with a taper, and a removable cap with a cutting edge for pressure-reduced penetration of the impression material and the at least one penetrable portion of the wall of the tray body of the impression tray.

* * * * *

UNITED STATES PATENT AND TRADEMARK OFFICE
CERTIFICATE OF CORRECTION

PATENT NO.        : 8,465,281 B2
APPLICATION NO. : 11/579707
DATED             : June 18, 2013
INVENTOR(S)       : Haselhuhn et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1198 days.

Signed and Sealed this
Eighth Day of September, 2015

Michelle K. Lee
*Director of the United States Patent and Trademark Office*